(12) United States Patent
Teramoto et al.

(10) Patent No.: US 8,802,412 B2
(45) Date of Patent: Aug. 12, 2014

(54) POLYNUCLEOTIDES HAVING PROMOTER ACTIVITY

(75) Inventors: Hiroshi Teramoto, Fukuoka (JP); Hiroaki Udagawa, Chiba (JP); Rikako Taira, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/805,236

(22) PCT Filed: Jun. 23, 2011

(86) PCT No.: PCT/EP2011/060534
§ 371 (c)(1),
(2), (4) Date: Dec. 18, 2012

(87) PCT Pub. No.: WO2011/161208
PCT Pub. Date: Dec. 29, 2011

(65) Prior Publication Data
US 2013/0095550 A1    Apr. 18, 2013

Related U.S. Application Data

(60) Provisional application No. 61/359,187, filed on Jun. 28, 2010.

(30) Foreign Application Priority Data

Jun. 25, 2010   (EP) ..................................... 10167315

(51) Int. Cl.
*C12N 15/80*    (2006.01)

(52) U.S. Cl.
USPC ......................................... 435/189; 435/200

(58) Field of Classification Search
CPC ........... C12N 15/1131; C12N 15/1132; C12N 15/86; C12N 2710/16122; C12N 2710/16134; C12N 2740/13022; C12N 2740/13043; C12N 2740/15022; C12N 2740/16043; C12N 2760/16134
USPC .............................................. 435/189, 254.4
See application file for complete search history.

(56) References Cited

FOREIGN PATENT DOCUMENTS

WO    93-07277 A1    4/1993

OTHER PUBLICATIONS

Tian et al., Mutations in two amino acids in phyI1s from *Aspergillus niger* 113 improve its phytase activity. World J. Microbiol. Biotechnol. 26: 903-907, 2010, Published on line 25, Nov. 2009.*
Tian et al., Semi-rational site-directed mutagenesis of phyI1s from *Aspergillus niger* 113 at two residue to improve its phytase activity. Mol. Biol. Rep. 38: 977-982, 2011, Published on line 5, Jun. 2010.*
Radzio et al 1997, Process Biochem 32 (6), 529-539.
Kubodera et al, 2000, GenBank Access No. AF217503.
Minetoki et al, 1995, Biosci Biotech Biochem 59 (8), 1516-1521.
Sharma et al, 2009, World J Microbiol Biotechnol 25 (12), 2083-2094.
Shoji et al, 2005, Ferris Microbiol Lett 244 (1), 41-46.

* cited by examiner

*Primary Examiner* — Tekchand Saidha
*Assistant Examiner* — Rama P Ramanujam
(74) *Attorney, Agent, or Firm* — Robert L. Stames

(57) ABSTRACT

The present invention relates to isolated polynucleotides having promoter activity the use of the isolated polynucleotides for the production of a polypeptide. The invention also relates to nucleic acid constructs, vectors, and host cells comprising the polynucleotides as well as methods of producing a desired polypeptide using the polypeptide having promoter activity.

12 Claims, No Drawings

POLYNUCLEOTIDES HAVING PROMOTER ACTIVITY

CROSS-REFERENCE TO RELATED APPLICATIONS

This application is a 35 U.S.C. 371 national application of PCT/EP2011/060534 filed Jun. 23, 2011, which claims priority or the benefit under 35 U.S.C. 119 of European application no. 10167315.0 filed Jun. 25, 2010 and U.S. provisional application No. 61/359,187 filed Jun. 28, 2010, the contents of which are fully incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to polynucleotides having promoter activity. In particular the invention relates to polynucleotides having promoter activity in fungal host cells. The invention also relates to nucleic acid constructs, vectors, and host cells comprising the polynucleotides as well as methods of producing polypeptides using the polynucleotides of the invention.

2. Description of the Related Art

The recombinant production of a heterologous protein in a fungal host cell, particularly a filamentous fungal cell such as *Aspergillus*, may provide for a more desirable vehicle for producing the protein in commercially relevant quantities.

Recombinant production of a heterologous protein is generally accomplished by constructing an expression cassette in which the DNA coding for the protein is placed under the expression control of a promoter, excised from a regulated gene, suitable for the host cell. The expression cassette is introduced into the host cell. Production of the heterologous protein is then achieved by culturing the transformed host cell under inducing conditions necessary for the proper functioning of the promoter contained on the expression cassette.

Improvement of the recombinant production of proteins generally requires the availability of new regulatory sequences which are suitable for controlling the expression of the proteins in a host cell. The regulatory sequence could be a suitable promoter sequence, being able to direct transcription of a gene operably linked to the promoter sequence. The leader sequence is operably linked to the 5' terminus of the nucleotide sequence encoding the polypeptide.

Promoter sequences for filamentous fungal host cells may be obtained from the genes derived from for *Aspergillus oryzae* TAKA amylase and *Aspergillus nidulans* triose phosphate isomerase.

It is an object of the present invention to provide new promoters for use in fungal host cells and further to provide improved methods for producing a polypeptide in a fungal host cell using the new promoters.

SUMMARY OF THE INVENTION

In a first aspect the invention relates to an isolated polynucleotide having promoter activity, selected from the group consisting of:

(a) a polynucleotide comprising a nucleotide sequence having promoter activity having at least 60%, more preferably at least 65%, more preferably at least 70%, more preferably at least 75%, more preferably at least 80%, more preferably at least 85%, even more preferably at least 90%, and most preferably at least 95% sequence identity to the nucleotide sequence of SEQ ID NO: 1; and (b) a polynucleotide having promoter activity that hybridizes under at least low stringency conditions, more preferably at least medium stringency conditions, even more preferably at least medium-high stringency conditions, most preferably at least high stringency, and even most preferably at least very high stringency conditions with the nucleotide sequence of SEQ ID NO: 1, or a full-length complementary strand thereof.

In a further aspect the invention relates to nucleic acids constructs, expression vectors and/or host cells comprising the the nucleotide sequence of the invention operably linked to a coding sequence with which the nucleotide sequence of the invention is not connected in its natural form.

Finally, the invention related to a method of producing a desired polypeptide, comprising: (a) cultivating a host cell comprising a nucleic acid construct comprising the nucleotide of the invention operably linked to a coding sequence encoding a desired polypeptide under conditions conducive for production of the polypeptide; and (b) recovering the polypeptide.

Definitions

Sequence Identity: The relatedness between two nucleotide sequences is described by the parameter "sequence identity".

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

The length of the alignment is preferably at least 10 nucleotides, preferably at least 25 nucleotides more preferred at least 50 nucleotides and most preferred at least 100 nucleotides.

Subsequence: The term "subsequence" is defined herein as a nucleotide sequence having one or more (several) nucleotides deleted from the 5' and/or 3' end of the nucleotide sequence of SEQ ID NO: 1; or a homologous sequence thereof; wherein the subsequence has promoter activity. In one aspect, a subsequence contains at least 10 nucleotides, more preferably at least 25 nucleotides, more preferably at least 50 nucleotides, more preferred at least 100 nucleotides, even more preferred at least 200 nucleotides and most preferred at least 500 nucleotides of the nucleotide sequence of SEQ ID NO: 1 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the function of the polynucleotide) or they may have an impact on the function of the polynucleotide. An allelic variant of a polynucleotide having promoter activity is a polynucleotide obtained from an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide. Each control sequence may be native or foreign to the nucleotide sequence encoding a polypeptide to be expressed or native or foreign to each other. Such control sequences include, but are not limited to, a leader, polyadenylation sequence, propeptide sequence, signal peptide sequence, and transcription terminator. At a minimum, the control sequences include transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of a polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide having promoter sequence of the invention and a polynucleotide encoding a polypeptide and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

DETAILED DESCRIPTION OF THE INVENTION

Polynucleotides having Promoter Activity

For the present invention a polynucleotide having promoter activity in intended to mean a nucleotide sequence that is recognized by a host cell for expression of a polynucleotide operably linked to the polynucleotide having promoter activity. A polynucleotide having promoter activity may be any nucleotide sequence that shows transcriptional activity in the host cell of choice including mutant, truncated, and hybrid promoters, and may be obtained from genes encoding extracellular or intracellular polypeptides either homologous or heterologous to the host cell.

A polynucleotide having promoter activity of the present invention may be obtained from microorganisms of any genus. For purposes of the present invention, the term "obtained from" as used herein in connection with a given source shall mean that the polynucleotide having promoter activity can be isolated from the source or by a strain in which the nucleotide sequence from the source has been inserted.

The polynucleotide having promoter activity of the invention comprises or consists of polynucleotrides having at least 60% sequence identity to SEQ ID NO: 1, preferably at least 70% sequence identity, more preferred at least 80% sequence identity, more preferred at least 90% sequence identity, even more preferred at least 95% sequence identity, still more preferred at least 97% sequence identity and most preferred at least 98% sequence identity.

The length of the alignment between the polynucleotide having sequence identity to SEQ ID NO: 1 and SEQ ID NO: 1 is preferably at least 10 nucleotids, more preferred at least 25 nucleotides even more preferred at least 50 nucleotides and most preferred at least 100 nucleotides.

A particular preferred promoter of the invention is the promoter having SEQ ID NO: 1 or allelic variants thereof. This promoter may be isolated from the calatase gene, catB, found in *Aspergillus niger*.

A polynucleotide having promoter activity of the present invention may obtained from a fungus, such as a yeast such as *Candida*, *Kluyveromyces*, *Pichia*, *Saccharomyces*, *Schizosaccharomyces*, or *Yarrowia*; or more preferably from a filamentous fungus such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria*.

In another preferred aspect, the polynucleotide having promoter activity of the invention is obtained from *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thiela-

*via spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride.*

In another preferred aspect, the polynucleotide having promoter activity is obtained from an *Aspergillus niger* or *Aspergillus oryzae.*

In a most preferred aspect, the polynucleotide having promoter activity of the invention is obtained from *Aspergillus niger.*

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polynucleotides having promoter activity may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic library of such a microorganism. Once a polynucleotide having promoter activity has been detected, the polynucleotide can be isolated or cloned by utilizing techniques that are well known to those of ordinary skill in the art (see, e.g., Sambrook et al., 1989, supra).

The techniques used to isolate or clone a polynucleotide having promoter activity are known in the art and include but are not limited to isolation from genomic DNA and various promoter trapping techniques. The cloning of the polynucleotides of the present invention from such genomic DNA can be effected, e.g., by using the well known polymerase chain reaction (PCR). See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus,* or another or related organism and thus, for example, may be an allelic or species variant of the polynucleotide having promoter activity of the invention.

The present invention also relates to isolated polynucleotides having promoter activity comprising or consisting of nucleotide sequences having a degree of sequence identity to the sequence of SEQ ID NO: 1 of preferably at least 60%, more preferably at least 65%, more preferably at least 70%, more preferably at least 75%, more preferably at least 80%, more preferably at least 85%, even more preferably at least 90%, more preferably at least 95%, and most preferably at least 96%, at least 97%, at least 98%, or at least 99%.

The present invention also relates to isolated polynucleotides having promoter activity of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the sequence of SEQ ID NO: 1, (ii) a full-length complementary strand of (i); or allelic variants and subsequences thereof (Sambrook et al., 1989, supra), as defined herein.

The present invention also relates to isolated polynucleotides having promoter activity obtained by (a) hybridizing a population of DNA under very low, low, medium, medium-high, high, or very high stringency conditions with (i) the mature polypeptide coding sequence of SEQ ID NO: 1, (ii) a full-length complementary strand of (i); and (b) isolating the hybridizing polynucleotide, having promoter activity.

Nucleic Acid Constructs

The present invention also relates to nucleic acid constructs comprising an isolated polynucleotide of the present invention operably linked to one or more (several) control sequences that direct the expression of a coding sequence in a suitable host cell under conditions compatible with the control sequences.

An isolated polynucleotide having promoter activity of the present invention may be manipulated in a variety of ways to provide for expression of a polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus* oryzae TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence having promoter activity of the invention would be operably linked with the regulatory sequence.

Expression Vectors

The present invention also relates to recombinant expression vectors comprising a polynucleotide of the present invention, a coding sequence a desired polypeptide, and transcriptional and translational stop signals. The various nucleic acids and control sequences described herein may be joined together to produce a recombinant expression vector that may include one or more (several) convenient restriction sites to allow for insertion or substitution of the nucleotide sequences at such sites. Alternatively, a polynucleotide sequence of the present invention may be used by inserting the nucleotide sequence or a nucleic acid construct comprising the sequence into an appropriate vector for expression of a coding sequence. In creating the expression vector, the coding sequence is located in the vector so that the coding sequence is operably linked with the appropriate control sequences for expression as well as the polunucleotide having promoter activity of the invention.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of origins of replication useful in a filamentous fungal cell are AMA1 and ANSI (Gems et al., 1991, Gene 98: 61-67; Cullen et al., 1987, Nucleic Acids Research 15: 9163-9175; WO 00/24883). Isolation of the AMA1 gene and construction of plasmids or vectors comprising the gene can be accomplished according to the methods disclosed in WO 00/24883.

More than one copy of a nucleis acid construct comprising then polynucleotide having promoter activity of the present invention may be inserted into a host cell to increase production of a desired gene product. An increase in the copy number of the nucleic acid construct can be obtained by integrating at least one additional copy of the sequence into the host cell genome or by including an amplifiable selectable marker gene with the polynucleotide where cells containing amplified copies of the selectable marker gene, and thereby additional copies of the polynucleotide having promoter activity of the invention, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention operably linked to one or more (several) control sequences that direct the production of a desired polypeptide. A construct or vector comprising a polynucleotide of the present invention is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide, e.g., a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzian urn*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* land *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

In the production methods of the present invention, the cells are cultivated in a nutrient medium suitable for providing transcriptional activity from the polynucleotide having promoter activity of the invention. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing transcriptional activity of the polynucleotide having promoter activity of the invention. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If nucleic acid construct comprising the polynucleotide having promoter activity of the invention is designed to express a desired polypeptide and the polypeptide is secreted into the nutrient medium, the polypeptide can be recovered directly from the medium. Such a polypeptide may be recovered using methods known in the art. For example, the polypeptide may be recovered from the nutrient medium by conventional procedures including, but not limited to, centrifugation, filtration, extraction, spray-drying, evaporation, or precipitation.

The present invention is further described by the following examples that should not be construed as limiting the scope of the invention.

EXAMPLES

Chemicals used as buffers and substrates were commercial products of at least reagent grade.

Materials and Methods

Methods

Molecular cloning techniques are described in Sambrook, J., Fritsch, E. F., Maniatis, T. (1989) Molecular cloning: a laboratory manual (2nd edn.) Cold Spring Harbor Laboratory, Cold Spring Harbor, N.Y.

Enzymes

Enzymes for DNA manipulations (e.g. restriction endonucleases, ligases etc.) are obtainable from New England Biolabs, Inc. and were used according to the manufacturer's instructions.

Media and Reagents

Chemicals used for buffers and substrates were commercial products of analytical grade.

Cove-N(tf) plates are composed of 342.3 g of sucrose, 20 ml of Cove salt solution, 3 g of NaNO$_3$, and 30 g of noble agar, water to 1 litre.

Cove-N plates are composed of 30 g of sucrose, 20 ml of Cove salt solution, 3 g of NaNO$_3$, and 30 g of noble agar, water to 1 litre.

COVE salt solution is composed of 26 g KCl, 26 g MgSO$_4$.7H$_2$O, 76 g KH$_2$PO$_4$ and 50 ml Cove trace metals, water to 1 litre.

Trace metal solution for COVE is composed of 0.04 g NaB$_4$O$_7$.10H$_2$O, 0.4 g of CuSO$_4$.5H$_2$O, 1.2 g of FeSO$_4$.7H$_2$O, 1.0 g of MnSO$_4$H2O, 0.8 g of Neutral amylase II MoO$_2$.2H$_2$O, and 10.0 g of ZnSO$_4$.7H20, water to 1 litre.

Cove-N top agarose is composed of 342.3 g of Sucrose, 20 ml of COVE salt solution, 3 g of NaNO$_3$, and 10 g of low melt agarose, water to 1 litre.

amyloglycosidase trace metal solution is composed of 6.8 g ZnCl$_2$.7H$_2$O, 2.5 g CuSO$_4$.5H$_2$O, 0.24 g NiCl$_2$.6H$_2$O, 13.9 g FeSO$_4$.7H$_2$O, 13.5 g MnSO$_4$.H$_2$O and 3 g citric acid, water to 1 litre.

YPG is composed of 4 g of yeast extract, 1 g of KH$_2$PO$_4$, 0.5 g of MgSO$_4$.7H$_2$O and 15 g of Glucose (pH 6.0), water to 1 litre.

STC buffer is composed of 0.8 M of sorbitol, 25 mM of Tris (pH 8), and 25 mM of CaCl$_2$, water to 1 litre.

STPC buffer is composed of 40% PEG4000 in STC buffer.

MLC is composed of 40 g Glucose, 50 g Soybean powder, 4 g/Citric acid (pH 5.0), water to 1 litre.

MSS is composed of 70 g Sucrose, 100 g Soybean powder (pH 6.0), water to 1 litre.

MU-1 is composed 260 g of Maltodextrin, 3 g of MgSO$_4$.7H$_2$O, 5 g of KH$_2$PO$_4$, 6 g of K$_2$SO$_4$, amyloglycosidase trace metal solution 0.5 ml and urea 2 g (pH 4.5), water to 1 litre.

Purchased Material (*E. coli*, Plasmid and Kits)

*E. coli* DH5-alpha (Toyobo) is used for plasmid construction and amplification. The commercial plasmids/vectors TOPO cloning kit (Invitrogen) and pBlue script II SK-(Stratagene #212206). are used for cloning of PCR fragments. Amplified plasmids are recovered with Qiagen® Plasmid Kit (Qiagen). Ligation is done with DNA ligation kit (Takara) or T4 DNA ligase (Boehringer Mannheim). Polymerase Chain Reaction (PCR) is carried out with Expand™ PCR system (Boehringer Mannheim). QIAquick™ Gel Extraction Kit (Qiagen) is used for the purification of PCR fragments and extraction of DNA fragment from agarose gel.

Strains

*Aspergillus nidulans* strain NRRL 1092 was used as donor of xylanase gene promoter and nitrate reductase gene terminator.

The expression host strain *Aspergillus niger* QMJi016-14-1 was isolated by Novozymes and is a derivative of *Aspergillus niger* NN049184 which was isolated from soil. QMJi016-14-1 is genetically modified to disrupt expression of ku70, oah and pyrG.

The expression host strain *Aspergillus niger* NN059180 (pyrG-) was isolated by Novozymes and is a derivative of *Aspergillus niger* NN049184 which was isolated from soil. NN059180 is genetically modified to disrupt expression of amyloglycosidase activities. Neutral amylase I gene in *Aspergillus niger* NN059180 is interrupted with *E. coli* Hygromicin B phosphotransferase gene.

*Aspergillus oryzae* Bech2 is described in WO 00/39322 example 1.

*Aspergillus oryzae* strain #13-1 described in WO2006/069289 is isolated by Novozymes.

*Aspergillus oryzae* IFO 4177 described in WO2006/069289 is isolated by Novozymes and is available from Institute for Fermentation, Osaka (IFO) Culture Collection of Microorganisms, 17-85, Juso-honmachi, 2-chome, Yodogawa-ku, Osaka 532-8686, Japan.

Plasmids

The expression cassette plasmid pJaL790 (described in patent publication WO2005070962)

The expression cassette plasmid pHUda440 (described in patent publication WO2006/069289)

The expression cassette plasmid pCBPhycutiprepro (described in patent publication WO2008/017646)

pJaL574 is described in example 9 in WO07045248

Transformation of *Aspergillus niger*

Transformation of *Aspergillus* species can be achieved using the general methods for yeast transformation. The preferred procedure for the invention is described below.

*Aspergillus niger* host strain was inoculated to 100 ml of YPG medium supplemented with 10 mM uridine and incubated for 16 hrs at 32° C. at 80 rpm. Pellets were collected and washed with 0.6 M KCl, and resuspended 20 ml 0.6 M KCl containing a commercial β-glucanase product (GLUCANEX™, Novozymes A/S, Bagsværd, Denmark) at a final concentration of 20 mg per ml.

The suspension was incubated at 32° C. at 80 rpm until protoplasts were formed, and then washed twice with STC buffer. The protoplasts were counted with a hematometer and resuspended and adjusted in an 8:2:0.1 solution of STC:STPC:DMSO to a final concentration of $2.5 \times 10^7$ protoplasts/ml. Approximately 4 pg of plasmid DNA was added to 100 μl of the protoplast suspension, mixed gently, and incubated on ice for 30 minutes. One ml of SPTC was added and the protoplast suspension was incubated for 20 minutes at 37° C. After the addition of 10 ml of 50° C. Cove-N top agarose, the reaction was poured onto Cove-N (if) agar plates and the plates were incubated at 32° C. for 5 days.

PCR Amplification

| | | |
|---|---|---|
| 5 × PCR buffer (incl.MgCl$_2$) | 20 μl | |
| 2.5 mM dNTP mix | 10 μl | |
| Forward primer (100 μM) | 1 μl | |
| Reverse primer (100 μM) | 1 μl | |
| Expand High Fidelity polymerase (Roche) | 1 μl | |
| Template DNA | 1 μl | |
| Distilled water to | 100 μl | |

PCR Conditions

| | | |
|---|---|---|
| 94 C. | 2 min | 1 cycle |
| 92 C. | 1 min | |
| 55 C. | 1 min | 30 cycles |
| 72 C. | 1-2 min | |
| 72 C. | 7 min | 1 cycle |

SF Cultivation for Glucoamylase Production

Spores of the selected transformants were inoculated in 100 ml of MLC media and cultivated at 30° C. for 2 days. 10 ml of MLC was inoculated to 100 ml of MU-1 medium and cultivated at 30° C. for 7 days. The supernatant was obtained by centrifugation.

SF Cultivation for Phytase Production

Spores of the selected transformants were inoculated in 100 ml of MSS media and cultivated at 30° C. for 2 days. 10 ml of MSS was inoculated to 100 ml of MU-1 medium and cultivated at 32° C. for 3 days. The supernatant was obtained by centrifugation.

Southern Hybridization

Mycelia of the selected transformants were harvested from overnight culture in 100 ml YPG medium, rinsed with distilled water, dried and frozen at −80° C. Ground mycelia were incubated with Proteinase K and RNaseA at 65° C. for 1 hrs.

Genome DNA was recovered by phenol/CHCl3 extraction twice followed by EtOH precipitation and resuspended with distilled water.

Non-radioactive probes were synthesized using a PCR DIG probe synthesis kit (Roche Applied Science, Indianapolis Ind.) followed by manufacture's instruction. DIG labeled probes were gel purified using a QIAquick™ Gel Extraction Kit (QIAGEN Inc., Valencia, Calif.) according to the manufacturer's instructions.

Five micrograms of genome DNA was digested with appropriate restriction enzymes completely for 16 hours (40 μl total volume, 4U enzyme/μl DNA) and run on a 0.8% agarose gel. The DNA was fragmented in the gel by treating with 0.2 M HCl, denatured (0.5M NaOH, 1.5M NaCl) and neutralized (1 M Tris, pH7.5; 1.5M NaCl) for subsequent transfer in 20×SSC to Hybond N+ membrane (Amersham). The DNA was UV cross-linked to the membrane and prehybridized for 1 hour at 42° C. in 20 ml DIG Easy Hyb (Roche Diagnostics Corporation, Mannheim, Germany). The denatured probe was added directly to the DIG Easy Hyb buffer and an overnight hybridization at 42° C. was done. Following the post hybridization washes (twice in 2×SSC, room temperature, 5 min and twice in 0.1×SSC, 68° C., 15 min. each), chemiluminescent detection using the DIG detection system and CPD-Star (Roche) was done followed by manufacture's protocol. The DIG-labeled DNA Molecular Weight Marker II (Roche) was used for the standard marker.

Phytase Assay

1 FYT-V is the amount of enzyme which releases 1 μmol inorganic phosphate per minute under the standard conditions below. The phytase activity (FYT-V/ml) is measures relative to a Novozymes Bio-Feed Phytase standard.

| Reaction conditions | |
|---|---|
| pH | 5.5 |
| Temperature | 37° C. |
| Substrate concentration | 5.0 mM |
| Wavelength | 405 nm |
| Incubation time | 15 min |

75 μl/well enzyme solution (diluted in 0.25M Sodium acetate, 0.005% Tween-20, pH5.5) is dispensed in a 96-well microtiter plates, then 75 μl substrate (Sodium phytate from rice (Aldrich 274321; MW 923.8) 10 mg/ml in 0.25 M Na-acetate buffer pH 5.5) is added and the plate is incubated for 15 min at 37° C. The reaction was stopped by adding 75 μl stop reagent (2.5% Ammonium hepta-morybdate and 0.06% ammonium vanadate in 10.9% nitric acid).

Absorbance at 405 nm is measured on 100 μl samples in 96 well microtiter plates.

Glucoamylase Activity

Glucoamylase activity is measured in AmyloGlucosidase Units (AGU). The AGU is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

Amyloglycosidase Incubation:

Substrate: maltose 23.2 mM

Buffer: acetate 0.1 M pH: 4.30 ±0.05
Incubation temperature: 37° C.±1
Reaction time: 5 minutes
Enzyme working range: 0.5-4.0 AGU/mL
Color Reaction:
GlucDH: 430 U/L
Mutarotase: 9 U/L
NAD: 0.21 mM
Buffer: phosphate 0.12 M; 0.15 M NaCl
pH: 7.60±0.05
Incubation temperature: 37° C.±
Reaction time: 5 minutes
Wavelength: 340 nm Example 1

Expression of Phytase Using the Catalase Promoter

Construction of pIH142
Aiming to integrate a single copy of enzyme expression cassette, pIH142 was contracted having the 5' and 3' flanking sequence of neutral amylase gene.
The primer sets of 5NA1 F and 5NA1 R, and 3NA1 F and 3NA1 R were designed to amplify *Aspergillus niger* 5' and 3' flanking region of neutral amylase I (NAI) gene respectively based on the nucleotide sequences information in the genome database of *Aspergillus niger*.

```
5NA1F:
                                             (SEQ ID NO: 2)
gtttaaacctatctgttccctccccccc 5NA1R:
                                             (SEQ ID NO: 3)
tttactagtgctagctgacttctatataaaaatgagta 3NA1F:
                                             (SEQ ID NO: 4)
tttctagagtatatgatggtactgctattc 3NA1R:
                                             (SEQ ID NO: 5)
gcggccgcgcattctcctagttactgatgact
```

A PCR reaction with the genome DNA of the *Aspergillus niger* NN059180 as template was performed with these primer pair set. The 1.8 kb and 1.4 kg product bands were purified on a 1.0% agarose gel and used for the construction of pIH142. Beside, the plasmid pIH142 harbours the cDNA clone of glucoamylase gene amplified from *Aspergillus oryzae* strain #13-1(described in WO2006069289, isolated by Novozymes) using a primer pair of TOGA-F and TOGA-R.

```
TCGA-F:
                                             (SEQ ID NO: 6)
tgggggatccaccatgcgtttcacgctcct TCGA-R:
                                             (SEQ ID NO: 7)
ctcgagttaattaactaccgccaggtgtcgttc
```

The amplified glucoamylase gene was fused to the modified NA2 promoter from pJaL790. The plasmid pIH142 also contains a pyrG gene from *Aspergillus nidulans* NRRL1092 as a selection marker gene.
Construction of prika156
A part of the phytase gene including signal sequence or the rest part of the phytase gene was amplified with primer pairs, p384 and p387 or p385 and p386, using pCBPhy-cutipreproas template. Both obtained PCR fragments were recovered from agarose gel. Then, using the PCR fragments amplified with p384 and p387, and p385 and p386, SOE-PCR (splicing by overlap extension PCR) was carried out with a primer pair of p384 and p386. The obtained PCR flagment was recovered from agarose gel and digested with NheI and PacI. The recovered 1.3 kb fragment was ligated to NheI and PacI digested pIH142 to replace the glucoamylase gene. The ligation mixture was transformed into *E. coli* DH5a to create the expression plasmid prika156.

```
p384
                                             (SEQ ID NO: 8)
aagtcagctagccgtcggtgtgatggaaatcc p385
                                             (SEQ ID NO: 9)
tcaaaattgaggatttagtcttgatcggatctccaccatgaagttctt p386
                                             (SEQ ID NO: 10)
acccggatcttaattaactactctgtgac p387
                                             (SEQ ID NO: 11)
aagaacttcatggtggagatccgatcaagactaaatcctcaattttga
```

Construction of prika158
pHiTe8 (described in example 2) was digested by NheI and BamHI and the 1.0 kb region of *Aspergillus niger* catalase promoter in pHiTe8 was recovered from agarose gel and ligated into prika156 digested with BglII and NheI. The ligation mixture was transformed into *E. coli* DH5α to create the expression plasmid prika158 comprising an expression cassette of phytase based on the *Aspergillus niger* catalase promoter and the *Aspergillus niger* amyloglycosidase terminator (AMG terminator), the selective marker pyrG with its terminator repeats from *Aspergillus nidulans* 5' and 3' flanking region of *Aspergillus niger* neutral amylase I.
Construction of prika160
The 0.7 kb region of *Aspergillus oryzae* thiamine-regulatable thiA promoter was amplified by PCR with primer pairs, pPthiA F and pPthiA R, using genomic DNA of *Aspergillus oryzae* IFO 4177 as template

```
pPthiA F
                                             (SEQ ID NO: 12)
tcaggctagcaattgattacgggatcccat pPthiA R
                                             (SEQ ID NO: 13)
gagtagatctgtttcaagttgcaatgacta
```

The obtained PCR fragment containing *Aspergillus oryzae* thiA promoter was recovered from agarose gel, digested with NheI and BglII, and ligated into prika156 digested with BglII and NheI. The ligation mixture was transformed into *E. coli* DH5a to create the expression plasmid prika160 comprising an expression cassette of phytase based on the *Aspergillus oryzae* thiA promoter and the *Aspergillus niger* amyloglycosidase terminator (AMG terminator), the selective marker pyrG with its terminator repeats from *Aspergillus nidulans*, 5' and 3' flanking region of *Aspergillus niger* neutral amylase I.
prika158 and prika160 were introduced into *Aspergillus niger* strain QMJi016-14-1. Transformants were selected from the Cove-N (if) medium. Randomly selected transformants were inoculated onto Cove-N plates Strains which grew well on Cove-N plates were purified and subjected to Southern blotting analysis to confirm whether the expression cassette in prika158 and prika160 was integrated correctly at the defined loci as a single copy.
By the right integration event, a hybridized signal at the size of 2.9kb by NcoI digestion was shifted to 4.4 kb for transformants of prika158 and 4.1 kb for transformants of prika160 probed with 5'NA1 flanking region. And a 4.4 kb band for transformants of prika158 and 4.1 kb band for transformants of prika160 was detected probed with the phytase probe. Among the strains given the right integration events, three strains from the each construct, 158-14, 16, 18 and 160-6, 7, 12 were chosen. The phytase activities of the supernatants of each transformants were determined. Table 1 shows average phytase activity of the selected transformants, relative to the average activity of the transformants of prika160.

TABLE 1

Expression results

| Strain | Plasmid | Promoter | Phytase relative activities |
|---|---|---|---|
| 158-14,16,18 | prika158 | Catalase | 1.83 |
| 160-6, 7, 12 | prika160 | ThiA | 1.00 |

Example 2

Expression of Glucoamylase Controlled by the Catalase Promoter in *Aspergillus niger*

Construction of pHiTe8

The 1.0 kb region of *Aspergillus niger* catalase promoter was amplified by PCR with primer pairs, pHiTe08 F and pHiTe08 R using genomic DNA of *Aspergillus niger* NN059180 as template. The promoter sequence of the catalase gene was identified and the primers were designed based on the genome sequence database opened by JGI (http://genomejgi-psforg/Aspni5/Aspni5.home.html). The obtained 1.0 kb DNA fragment containing *Aspergillus niger* catalase promoter was recovered from agarose gel, and introduced into the modified version of pIH142 to replace the promoter region. Plasmid preparation was carried out in *E. coli* DH5α. Resulting plasmid was termed pHiTe8.

pHiTe08 F
(SEQ ID NO: 14)
ctagctagccgtcggtgtgatggaaatc pHiTe08 R
(SEQ ID NO: 15)
cgcggatccgaagggaagggggaagttg pHiTe8 comprised an expression cassette containing a glucoamylase gene controlled by the *Aspergillus niger* catalase promoter and the *Aspergillus niger* amyloglycosidase terminator (AMG terminator). The plasmid also carried the pyrG gene from *A. nidulans* as a selection marker gene.

Construction of HUda1032

The 0.7 kb region of *Aspergillus oryzae* thiamine-regulatable thiA promoter was amplified by PCR with primer pairs, pPthiA F and pPthiA R, using genome DNA of *Aspergillus oryzae* IFO 4177 as template The obtained PCR containing *Aspergillus oryzae* thiA promoter was recovered from agarose gel and introduced into a modified version of pIH142 to replace the promoter region. The ligation mixture was transformed into *E. coli* DH5a to create the expression plasmid pHUda1032 comprising an expression cassette containing a glucoamylase gene controlled by the *Aspergillus oryzae* thiA promoter and the *Aspergillus niger* amyloglycosidase terminator (AMG terminator), and the selective marker pyrG from *Aspergillus nidulans*.

pHiTe8 and pHUda1032 were introduced into *Aspergillus niger* NN059180. Transformants were selected from the minimum medium Cove-N (if).

Randomly selected transformants were inoculated onto Cove-N plates with 0.2g/l Hygromycin B, an agent which kills cells NOT expressing the *E. coli* Hygromicin B phosphotransferase gene located at NA1 locus of *Aspergillus niger* NN059180. Strains which could not grow on Cove-N plates with Hygromycin B were purified and subjected to Southern blotting analysis to confirm whether the expression cassette in pHiTe8 and pHUda1032 was integrated at the defined loci as a single copy.

By the right integration event, a hybridized signal at the size of 3.1 kb by NcoI digestion was shifted to 4.0 kb for transformants of pHiTe8, and 3.7 kb for transformants of pHUda1032 probed with 5'NA1 flanking region. And a 4.0 kb band for transformants of pHiTe8, and 3.7 kb band for transformants of pHUda1032 was detected probed with the glucoamylase probe. Among the strains given the right integration events, two strains from the each construct, 8-1, 6, and 1032-4, 5 were chosen. The glucoamylase activities of the supernatants of each transformants were determined. Table 2 shows average glucoamylase activity of the selected transformants, relative to the average activity of the transformants of pHUda1032.

TABLE 2

Expression results

| Strain | Plasmid | Promoter | Glucoamylase relative activities |
|---|---|---|---|
| 8-1,6 | pHiTe8 | Catalase | 1.32 |
| 1032-4, 5 | pHuda1032 | ThiA | 1.00 |

The invention claimed is:

1. A nucleic acid construct comprising an isolated polynucleotide having promoter activity operably linked to a heterologous coding sequence encoding a polypeptide, wherein the polynucleotide having promoter activity is selected from the group consisting of: (a) a polynucleotide comprising a nucleotide sequence having promoter activity having at least 95% sequence identity to the nucleotide sequence of SEQ ID NO: 1; and (b) a polynucleotide having promoter activity that hybridizes with the nucleotide sequence of SEQ ID NO: 1, or the full-length complement thereof, under stringency conditions defined as hybridization at 42° C. in DIG Easy Hyb buffer and washing twice in 2X SSC at room temperature for 5 minutes and twice in 0.1X SSC at 68° C. for 15 minutes each.

2. The nucleic acid construct of claim 1, wherein the polynucleotide having promoter activity comprises or consists of the nucleotide sequence of SEQ ID NO: 1; or a fragment thereof having promoter activity.

3. A recombinant expression vector comprising the nucleic acid construct of claim 1.

4. A recombinant host cell comprising the nucleic acid construct of claim 1.

5. A method of producing a desired polypeptide, comprising: (a) cultivating a recombinant host cell comprising a nucleic acid construct of claim 1 under conditions conducive for production of the polypeptide; and (b) recovering the polypeptide.

6. The method of claim 5 wherein the recombinant host cell is a filamentous fungus.

7. The method of claim 6, wherein the filamentous fungus is selected from the group consisting of Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes and Trichoderma.

8. The method of claim 6, wherein the filamentous fungus is selected from the group consisting of Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicil-

*lium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei* and *Trichoderma viride*.

9. The method of claim 5, wherein the polypeptide is an enzyme.

10. The method of claim 9, wherein the enzyme is selected from the group consisting of proteases, amylases, glucoamylases, lipases, cellulases, phytases, oxidative enzymes, oxidoreductases and pectinases.

11. The nucleic acid construct of claim 1, wherein the polynucleotide comprising a nucleotide sequence having promoter activity has at least 97% sequence identity to the nucleotide sequence of SEQ ID NO: 1.

12. The nucleic acid construct of claim 1, wherein the polynucleotide comprising a nucleotide sequence having promoter activity has at least 98% sequence identity to the nucleotide sequence of SEQ ID NO: 1.

* * * * *

SEQUENCE LISTING

<160> NUMBER OF SEQ ID NOS: 15

<210> SEQ ID NO 1
<211> LENGTH: 1005
<212> TYPE: DNA
<213> ORGANISM: Aspergillus niger

<400> SEQUENCE: 1
ctagccgtcg gtgtgatgga aatccagcac gttgcaggac caagaatccc cgggtgcggg    60
ggtgggctcg gctgaatggt ctgatcatac tggtttacta gtttactagt agttgctgta   120
aggaaccgtc gggggtgtta ttaatagctg gacttgcaga tggaacatga acatgtcctg   180

```
accattgtat ccctcgtgca tgaagcctgt ccctgggagt tggtagtagt tcatgcctga    240
ggtacggagt agtacaataa gtattggggc tacagctgct cacctgcaag gggaagacca    300
cttgtgttgt tgttgttatt gttgttgtta ttgttgttgt tattgttgtt gttattgttg    360
ttgttattgt tgttgttatt gttgttgtta ctgttattgt tattgttaca tgagtgggga    420
agaccaattg acaatcccga tactttccaa tcccttccg gatttcgtgc aacatcactg    480
cccattttga tattattatt attattatta ttatcatcat gattgtatta tggcacgaca    540
cgagtggaat tcacgtcatc gtctgccaag ccagtccctt tccatccaga cctcccgatt    600
accaagccct tccgccagtc agcttcgtcc tcctcctcat cgccaagcct gcccttcggc    660
cgggtcatgg acccccggc caatgagcaa cgcgccattg ccgtgtgtc tgcatctcga    720 tacgcatccc aggattcctt accgaaagat atcatcccaa gtaaggtaca cgcctggtat    780
cgaacaaaac atgctgggac ggacggctcc tacattcgtt actagtcata caatctagtc    840
aattagtagc tgctgccaat gccaatgcca atgccaatgc ctctctatat aattccctca    900 gttccccct ctcttctctc ctcctcccct cccttcctt ctcctctcac tgctccaatt    960
gcctcatctt ccctggacgt agtccaactt cccccttcc cttcg                    1005
```

<210> SEQ ID NO 2
<211> LENGTH: 28
<212> TYPE: DNA
<213> ORGANISM: Artificial
<220> FEATURE:
<223> OTHER INFORMATION: Primer 5NA1F

<400> SEQUENCE: 2

```
gtttaaacct atctgttccc tccccccc                                        28
```

<210> SEQ ID NO 3
<211> LENGTH: 38
<212> TYPE: DNA
<213> ORGANISM: Artificial
<220> FEATURE:
<223> OTHER INFORMATION: Primer 5NA1R

<400> SEQUENCE: 3

```
tttactagtg ctagctgact tctatataaa aatgagta                             38
```

<210> SEQ ID NO 4
<211> LENGTH: 30
<212> TYPE: DNA
<213> ORGANISM: Artificial
<220> FEATURE:
<223> OTHER INFORMATION: Primer 3NA1F

<400> SEQUENCE: 4

```
tttctagagt atatgatggt actgctattc                                      30
```

<210> SEQ ID NO 5
<211> LENGTH: 32
<212> TYPE: DNA
<213> ORGANISM: Artificial
<220> FEATURE:
<223> OTHER INFORMATION: Primer 3NA1R

<400> SEQUENCE: 5

```
gcggccgcgc attctcctag ttactgatga ct                                   32
```

```
<210> SEQ ID NO 6
<211> LENGTH: 30
<212> TYPE: DNA
<213> ORGANISM: Artificial
<220> FEATURE:
<223> OTHER INFORMATION: Primer TCGA-F

<400> SEQUENCE: 6
tgggggatcc accatgcgtt tcacgctcct                                    30

<210> SEQ ID NO 7
<211> LENGTH: 33
<212> TYPE: DNA
<213> ORGANISM: Artificial
<220> FEATURE:
<223> OTHER INFORMATION: Primer TCGA-R

<400> SEQUENCE: 7
ctcgagttaa ttaactaccg ccaggtgtcg ttc                                33

<210> SEQ ID NO 8
<211> LENGTH: 32
<212> TYPE: DNA
<213> ORGANISM: Artificial
<220> FEATURE:
<223> OTHER INFORMATION: Primer p384

<400> SEQUENCE: 8
aagtcagcta gccgtcggtg tgatggaaat cc                                 32

<210> SEQ ID NO 9
<211> LENGTH: 48
<212> TYPE: DNA
<213> ORGANISM: Artificial
<220> FEATURE:
<223> OTHER INFORMATION: Primer p385

<400> SEQUENCE: 9
tcaaaattga ggatttagtc ttgatcggat ctccaccatg aagttctt                48

<210> SEQ ID NO 10
<211> LENGTH: 29
<212> TYPE: DNA
<213> ORGANISM: Artificial
<220> FEATURE:
<223> OTHER INFORMATION: Primer p386

<400> SEQUENCE: 10
acccggatct taattaacta ctctgtgac                                     29

<210> SEQ ID NO 11
<211> LENGTH: 48
<212> TYPE: DNA
<213> ORGANISM: Artificial
<220> FEATURE:
<223> OTHER INFORMATION: Primer p387

<400> SEQUENCE: 11
aagaacttca tggtggagat ccgatcaaga ctaaatcctc aattttga                48

<210> SEQ ID NO 12
<211> LENGTH: 30
<212> TYPE: DNA
<213> ORGANISM: Artificial
<220> FEATURE:
<223> OTHER INFORMATION: Primer pPthiA F
```

```
<400> SEQUENCE: 12
tcaggctagc aattgattac gggatcccat                                         30

<210> SEQ ID NO 13
<211> LENGTH: 30
<212> TYPE: DNA
<213> ORGANISM: Artificial
<220> FEATURE:
<223> OTHER INFORMATION: Primer pPthiA R

<400> SEQUENCE: 13
gagtagatct gtttcaagtt gcaatgacta                                         30

<210> SEQ ID NO 14
<211> LENGTH: 28
<212> TYPE: DNA
<213> ORGANISM: Artificial
<220> FEATURE:
<223> OTHER INFORMATION: Primer pHiTe08 F

<400> SEQUENCE: 14
ctagctagcc gtcggtgtga tggaaatc                                           28

<210> SEQ ID NO 15
<211> LENGTH: 29
<212> TYPE: DNA
<213> ORGANISM: Artificial
<220> FEATURE:
<223> OTHER INFORMATION: Primer pHiTe08 R

<400> SEQUENCE: 15
cgcggatccg aagggaaggg gggaagttg                                          29
```